US009949739B2

(12) United States Patent
Tsukashima et al.

(10) Patent No.: US 9,949,739 B2
(45) Date of Patent: Apr. 24, 2018

(54) INTEGRAL WIPING SYSTEM AND METHOD

(71) Applicant: MicroVention. Inc, Aliso Viejo, CA (US)

(72) Inventors: Ross Tsukashima, San Diego, CA (US); Thomas Charles Sternweiler, Lake Forest, CA (US); Matthew J. Fitz, Vista, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 145 days.

(21) Appl. No.: 14/192,740

(22) Filed: Feb. 27, 2014

(65) Prior Publication Data

US 2014/0243883 A1 Aug. 28, 2014

Related U.S. Application Data

(60) Provisional application No. 61/770,198, filed on Feb. 27, 2013.

(51) Int. Cl.
*A61B 17/12* (2006.01)
*H01R 24/58* (2011.01)
(Continued)

(52) U.S. Cl.
CPC ........ *A61B 17/1214* (2013.01); *A61N 1/3752* (2013.01); *A61B 17/3462* (2013.01); *A61B 90/70* (2016.02); *A61B 2017/00017* (2013.01); *A61B 2017/0046* (2013.01); *A61B 2017/00115* (2013.01); *A61B 2017/00734* (2013.01); *A61B 2017/1205* (2013.01);
(Continued)

(58) Field of Classification Search
CPC ............ A61B 17/1214; A61B 17/3462; A61B 2017/0046; A61B 2017/1205; A61B 18/00; A61B 19/34; A61B 2562/227; H01R 24/38; H01R 24/542; H01R 31/06; H01R 24/58; H01R 13/514; H01R 13/5224; A61N 1/3752
USPC ...................................... 606/1, 200; 439/909
See application file for complete search history.

(56) References Cited

U.S. PATENT DOCUMENTS 5,176,140 A * 1/1993 Kami ....................... A61B 8/12
310/327
5,879,499 A 3/1999 Corvi
(Continued)

OTHER PUBLICATIONS

WIPO, U.S. International Search Authority, International Search Report and Written Opinion dated May 27, 2014 in International Patent Application No. PCT/US14/19155, 10pages.

*Primary Examiner* — Nathan J Jenness
(74) *Attorney, Agent, or Firm* — Inskeep IP Group, Inc.

(57) ABSTRACT

A grip assembly for an embolic delivery device is described, where said grip assembly includes an integral wiping system utilizing one or more wipers. The grip assembly is constructed and arranged to allow an embolic delivery device to be inserted into the grip quickly and easily, without shifting undue attention away from the patient to the device. The wiper or wipers prevent any fluids or debris that may be present on a proximal end of the embolic delivery device from entering the interior of the grip assembly, thereby preserving a clean environment for making solid electrical connections between contacts in the grip assembly and corresponding contacts on the embolic delivery device.

1 Claim, 7 Drawing Sheets

(51) Int. Cl.
*H01R 13/52* (2006.01)
*A61N 1/375* (2006.01)
*A61B 17/34* (2006.01)
*A61B 17/00* (2006.01)
*A61B 18/00* (2006.01)
*A61B 90/70* (2016.01)
*A61B 90/00* (2016.01)

(52) U.S. Cl.
CPC ............... *A61B 2018/00976* (2013.01); *A61B 2090/0808* (2016.02); *H01R 13/5224* (2013.01); *H01R 24/58* (2013.01); *H01R 2201/12* (2013.01)

(56) References Cited

U.S. PATENT DOCUMENTS

| | | | |
|---|---|---|---|
| 6,895,276 B2 * | 5/2005 | Kast | A61N 1/3752 439/909 |
| 2004/0111029 A1 * | 6/2004 | Bates | A61B 5/6826 600/437 |
| 2004/0181177 A1 | 9/2004 | Lee et al. | |
| 2006/0116584 A1 * | 6/2006 | Sudol | A61B 8/12 600/459 |
| 2008/0246231 A1 * | 10/2008 | Sjostedt | A61N 1/05 277/641 |
| 2010/0094395 A1 * | 4/2010 | Kellett | A61B 17/12022 623/1.11 |
| 2010/0199448 A1 | 8/2010 | Vazales et al. | |
| 2011/0059639 A1 * | 3/2011 | Dilmaghanian | H01R 13/5219 439/271 |
| 2011/0160824 A1 | 6/2011 | Ware et al. | |
| 2012/0315798 A1 * | 12/2012 | Poon | H01R 24/58 439/668 |
| 2013/0012046 A1 * | 1/2013 | Jullien | H01R 13/514 439/283 |
| 2013/0085520 A1 * | 4/2013 | Liang | A61B 17/12022 606/195 |

* cited by examiner

INTEGRAL WIPING SYSTEM AND METHOD

RELATED APPLICATIONS

This application claims priority to U.S. Provisional Application Ser. No. 61/770,198 filed Feb. 27, 2013 entitled Integral Wiping System, which is hereby incorporated herein by reference in its entirety.

BACKGROUND OF THE INVENTION

Embolic agents, such as coils, are often used to treat various intravascular conditions such as arteriovenous malformations (AVM), aneurysms, and fistulas. These agents fill the cavity and limit blood flow to these regions to reduce the chance of any bursting of the blood vessel. Embolic delivery systems must have a precise detachment mechanism to ensure proper and reliable detachment of the embolic agent once they are placed within the treatment site. One example of an embolic delivery system utilizes a pusher system and a grip system which the pusher system is inserted into. The grip system has a series of electrical contacts and when particular elements of the pusher system line up with the electrical contacts, a detachment sequence can be initialized by the user. This detachment sequence can be initiated by depressing a button on the grip system to release the embolic agent.

Blood, saline, or other fluids can cause contamination of these electrical contacts and may cause deterioration of the connection integrity between the pusher system and grip system. Deterioration of the connection integrity may result in the detachment sequence not functioning correctly. The inclusion of one or more wipers between the sets of contacts is one technique to reduce the potential of fluid to degrade these electrical contacts.

SUMMARY OF THE INVENTION

A grip assembly for an embolic delivery device is described, where the grip assembly includes an integral wiping system utilizing one or more wipers. The wipers are positioned and sized to engage a proximal end portion of an electrical medical device, such as an embolic delivery device, such that electrical contacts on the proximal end portion are wiped clean while being inserted into the grip assembly.

One aspect of the invention pertains to a grip assembly for a medical delivery system that includes a housing defining at least one channel sized to receive a proximal end of a medical delivery system; an electrical contact contained within the at least one channel and positioned to establish an electrical connection with an electrical contact on an external surface of the medical delivery system; and at least one annular wiper disposed within the housing and having a diameter smaller than a diameter of the proximal end of the medical delivery system, thereby creating an interference fit between the wiper and the medical delivery system, when the medical delivery system is inserted in the housing, that prevents dirt and/or fluid on the medical delivery system from passing by the wiper.

The at least one channel may comprise a plurality of channels. These channels may be coaxial in order to accommodate a medical delivery system that uses a single-pronged male connector configuration. This configuration is advantageous as it is easily inserted into the channels without regard to orientation.

In one aspect of the invention, the at least one wiper comprises a plurality of annular wipers, each of the wipers placed proximate one of the plurality of coaxial channels. These wipers and channels may be arranged in an alternating configuration.

Another aspect of the invention pertains to a grip assembly for controlling an electrical medical device comprising: at least one channel for receiving a proximal portion of the medical device; an electrical contact for establishing an electrical connection with a corresponding electrical contact on the proximal portion of the medical device; a power supply operably associated with the electrical contact for supplying the medical device with electricity; and at least one wiper coaxial with the at least one channel and having an inner diameter smaller than the at least one channel, such that when the medical device is inserted into the at least one channel, an interference fit is established between the medical device and the at least one wiper such that fluid and/or debris are prevented from entering the at least one channel.

Another aspect of the invention pertains to a method of establishing a clean electrical connection between a powered grip and a medical device inserted into the grip comprising providing at least one wiper in the grip, the wiper disposed to interfere with an electrical contact on a medical device being inserted into the grip without preventing the medical from being inserted into the grip.

BRIEF DESCRIPTION OF THE DRAWINGS

These and other aspects, features and advantages of the invention will be apparent and elucidated from the following description of embodiments of the present invention, reference being made to the accompanying drawings, in which.

DESCRIPTION OF EMBODIMENTS

Figure 1:
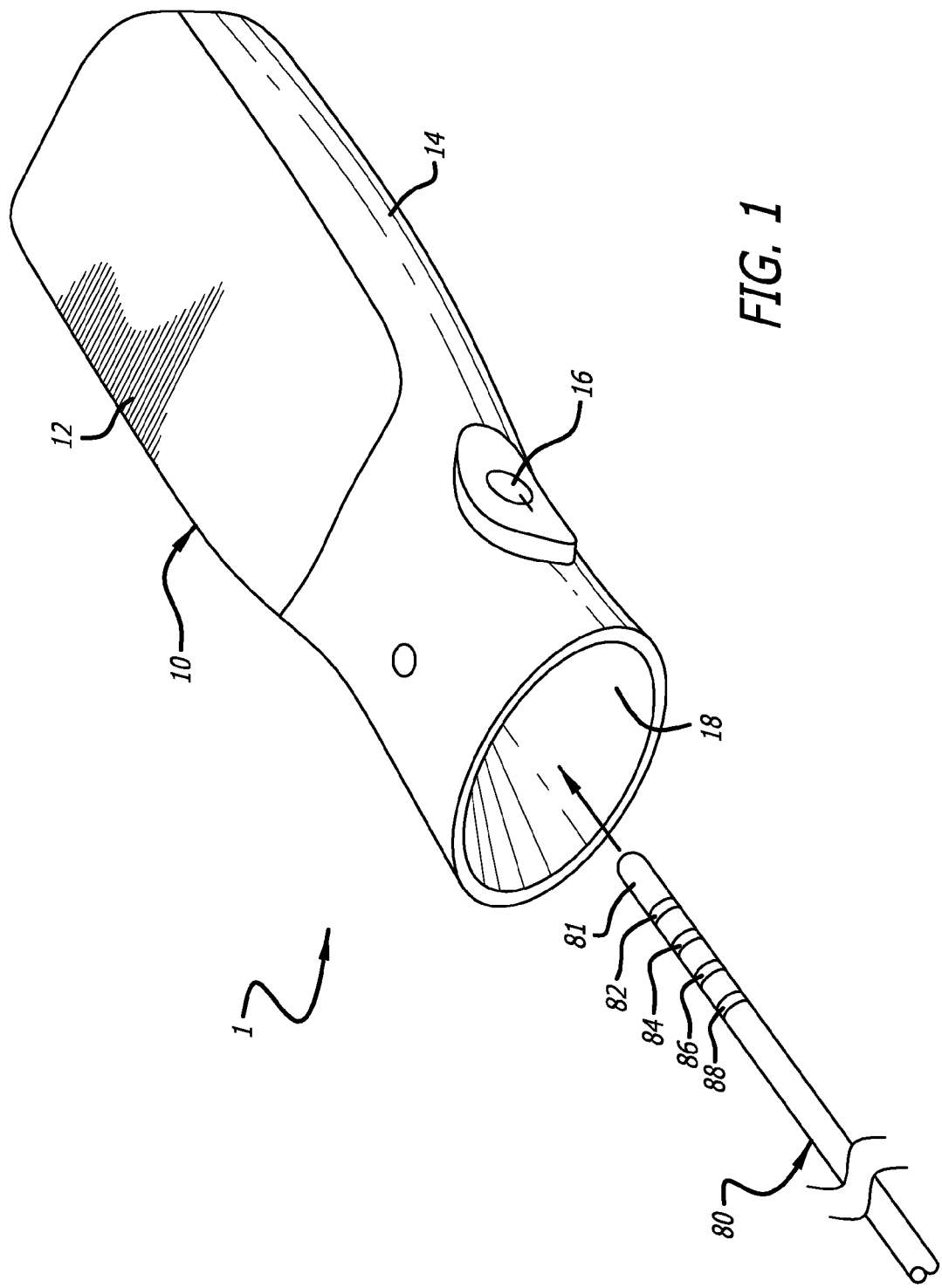
FIG. 1 is a perspective view of an embodiment of a grip system used as part of an embolic delivery system of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates a grip system 10 used as part of an embolic delivery system 1. The embolic delivery system 1 can be used, for example, to deliver embolic coils to a treatment site within the vasculature. The embolic delivery system 1 includes grip system 10, and a separate pusher system 80, which is inserted into grip system 10. The pusher system 80, which is connected to the embolic coil, can be inserted into the grip system 10 in order to facilitate deployment and detachment of the coil once the coil is delivered to a target site in the vasculature.

Figure 2:
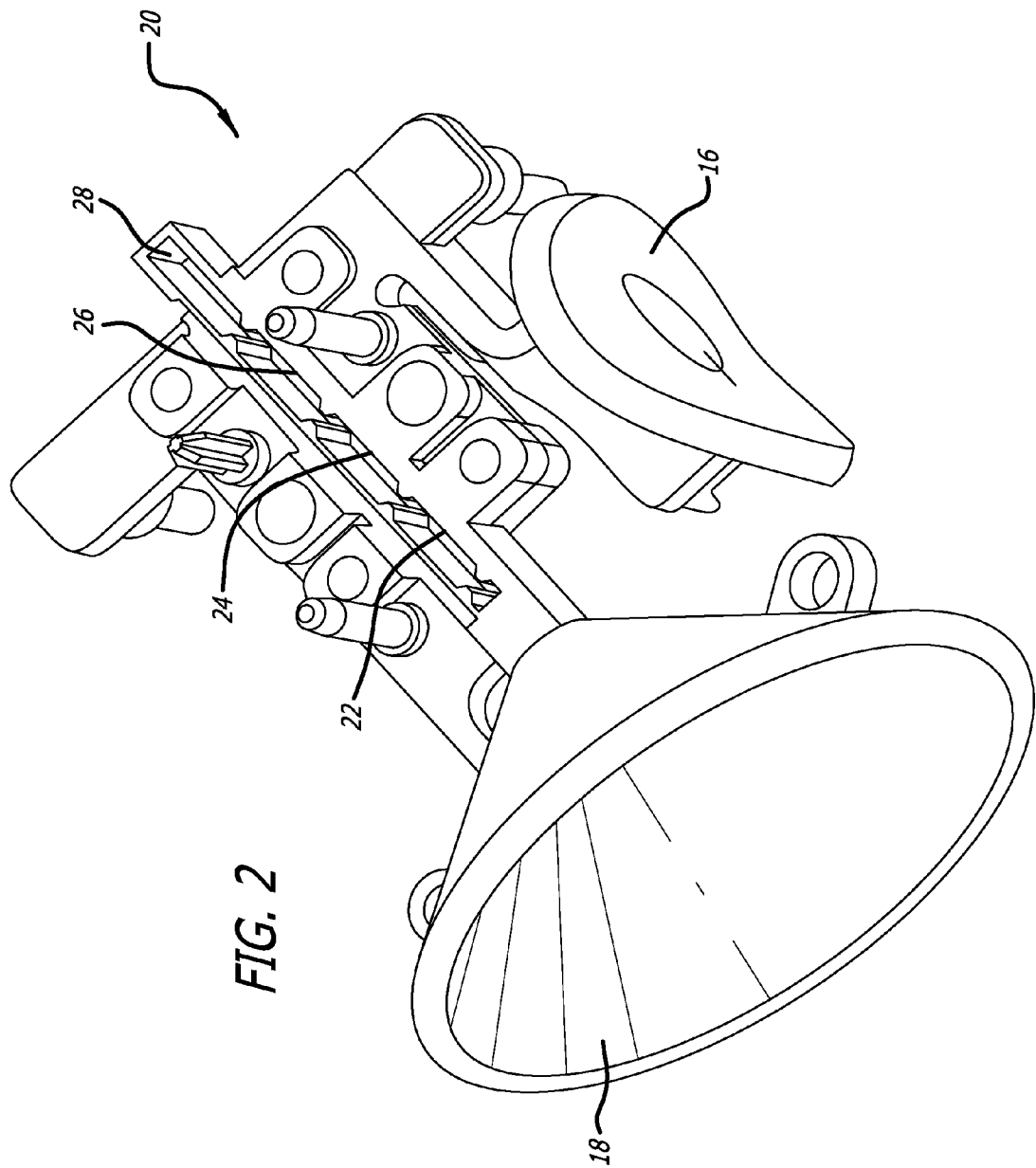
FIG. 2 is a perspective view of an embodiment of a pusher/grip connector of the invention.

FIGS. 3-7 detail the various components of the grip system 10. Externally, grip system 10 has a top housing 12 and bottom housing 14, and a funnel 18 that is part of a pusher/grip connector 20 that is best seen in FIG. 2. The pusher/grip connector 20 includes funnel 18, push button 16, and contains channels 22, 24, 26, 28. Although four channels are shown in FIG. 2, fewer or more channels can be used. These channels contain electrical connections which are used to detect when the pusher system 80 is correctly inserted into grip system 10 and when the embolic coils connected to the pusher system 80 can be detached within the vasculature.

In the embodiment shown in FIG. 2, the funnel 18 narrows to an opening that is coaxial with all four channels 22, 24, 26 and 28. This embodiment is designed for use with a pusher system 80, such as that shown in FIG. 1, that has a proximal end 81 having a plurality of external, circumferential electrical contacts 82, 84, 86 and 88. These contacts correspond to the channels 22, 24, 26 and 28. As such, when the proximal end 81 is pushed into the grip system 10, the funnel 18 directs the end 81 into the channels 22, 24, 26 and 28, without requiring the physician to shift focus away from the procedure being performed. An advantage to the axial design shown in FIG. 2 is that electrical connections are established without requiring a specific orientation of the pusher system 80 relative to the grip system 10.

Figure 3:
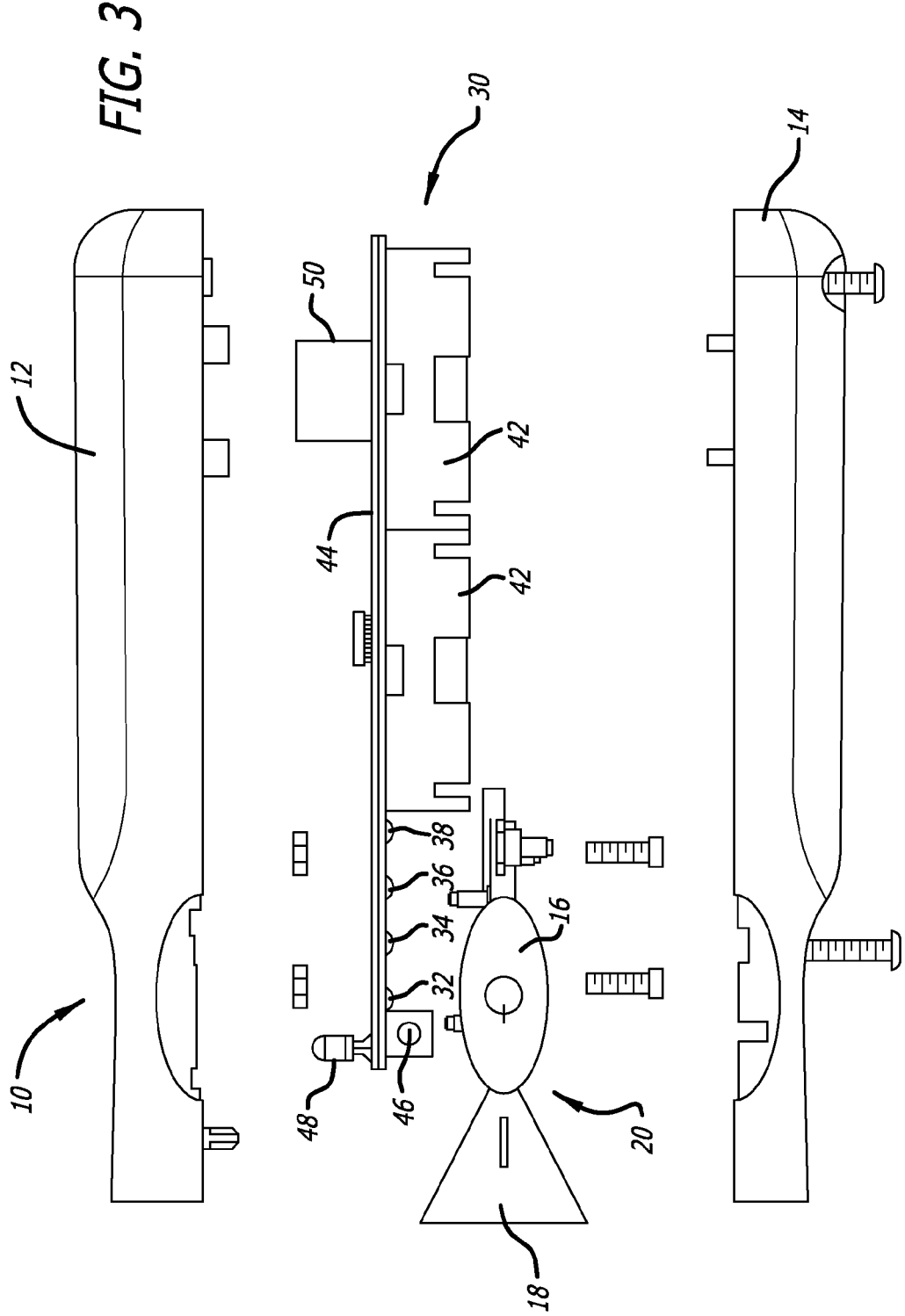
FIG. 3 is an exploded elevation of the embodiment of the grip system of FIG. 1.
Figure 4:
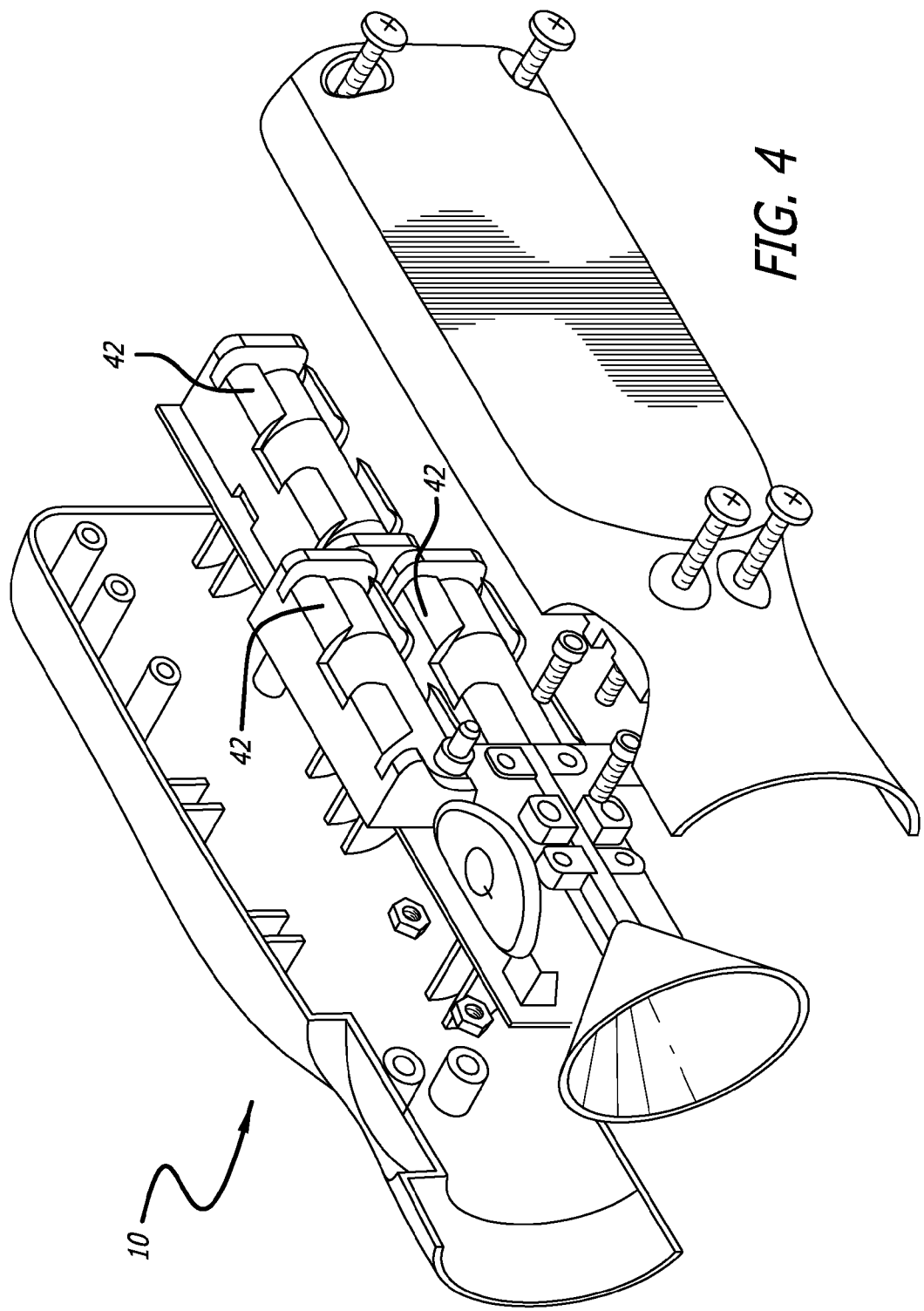
FIG. 4 is an exploded perspective view of the embodiment of the grip system of FIG. 1.

FIG. 3 is an exploded view of the grip system 10 from FIG. 1, showing more of the components. In addition to a top housing 12, bottom housing 14, and a pusher/grip connector 20, the grip system 10 also includes a control system 30. Control system 30 includes a power source 42, which is connected to circuit board 44. In one example, batteries can be used as a power source. In another example, three 12 Volt batteries can be used as a power source. In another example, a single 9 Volt battery can be used as a power source. FIG. 4 offers an exploded view showing an example of a power source, in this case a three battery power source 42.

FIG. 3 shows that control system 30 is connected to channels 22, 24, 26, 28 of the pusher/grip connector 20 via corresponding connectors 32, 34, 36, 38, which are inserted into the channels. Connectors 32, 34, 36, 38 are in turn connected to circuit board 44 as a part of control system 30.

Figure 5:
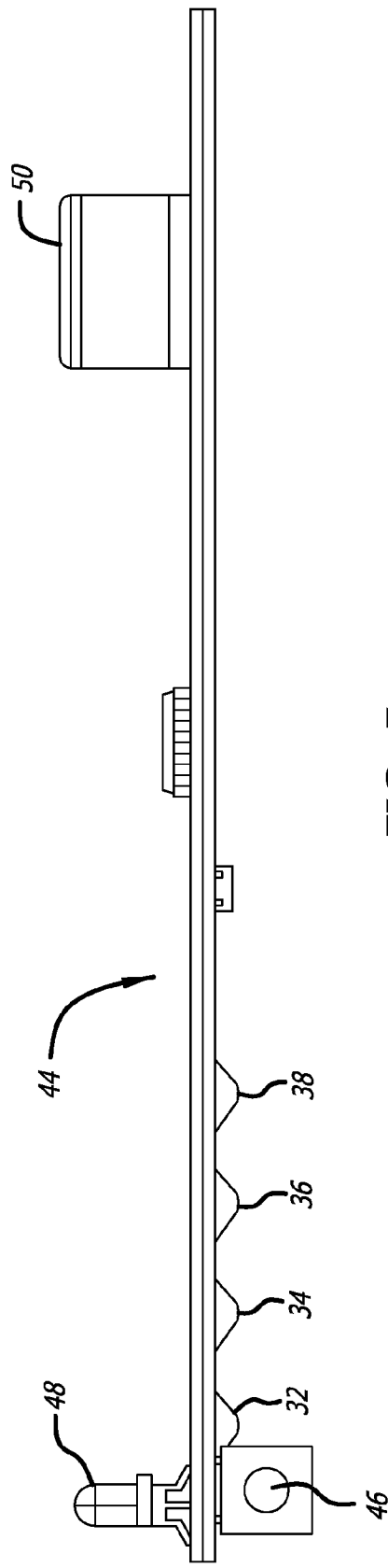
FIG. 5 is an elevation of an embodiment of a circuit board for use with the grip system of the invention.

Circuit board 44 is shown in greater detail in FIG. 5. The circuit board is connected to a back button 46. Back button 46 sits directly behind push button 16 of the pusher/grip connector 20. When the user pushes button 16, button 16 impinges back button 46 and this action is relayed through control system 30 via circuit board 44. Control system 30 includes a light 48 mounted to circuit board 44. Light 48 indicates when the leads within pusher/grip connector 20 are lined up correctly and the detachment sequence can be initiated. One color light (i.e. green) indicates the leads are lined up correctly and the detachment sequence can initiate. Another color light (i.e. red) indicates the detachment sequence cannot initiate as the signal is not registering properly. An audible alarm 50 is also included to audibly indicate that the detachment sequence can be initiated.

Connectors 32, 34, 36, 38 of control system 30 are mounted to circuit board 44 and fit within corresponding channels 22, 24, 26, 28 within pusher/grip connector 20. Although four connectors and four channels are shown in the Figures, fewer or more connectors and channels can be used. The connectors sense when a proper connection is made between the leads of the pusher system and the electrical connections of the pusher/grip connector, and thus when a detachment sequence can be initiated. The connectors can be made of any conductive metal.

Figure 6:
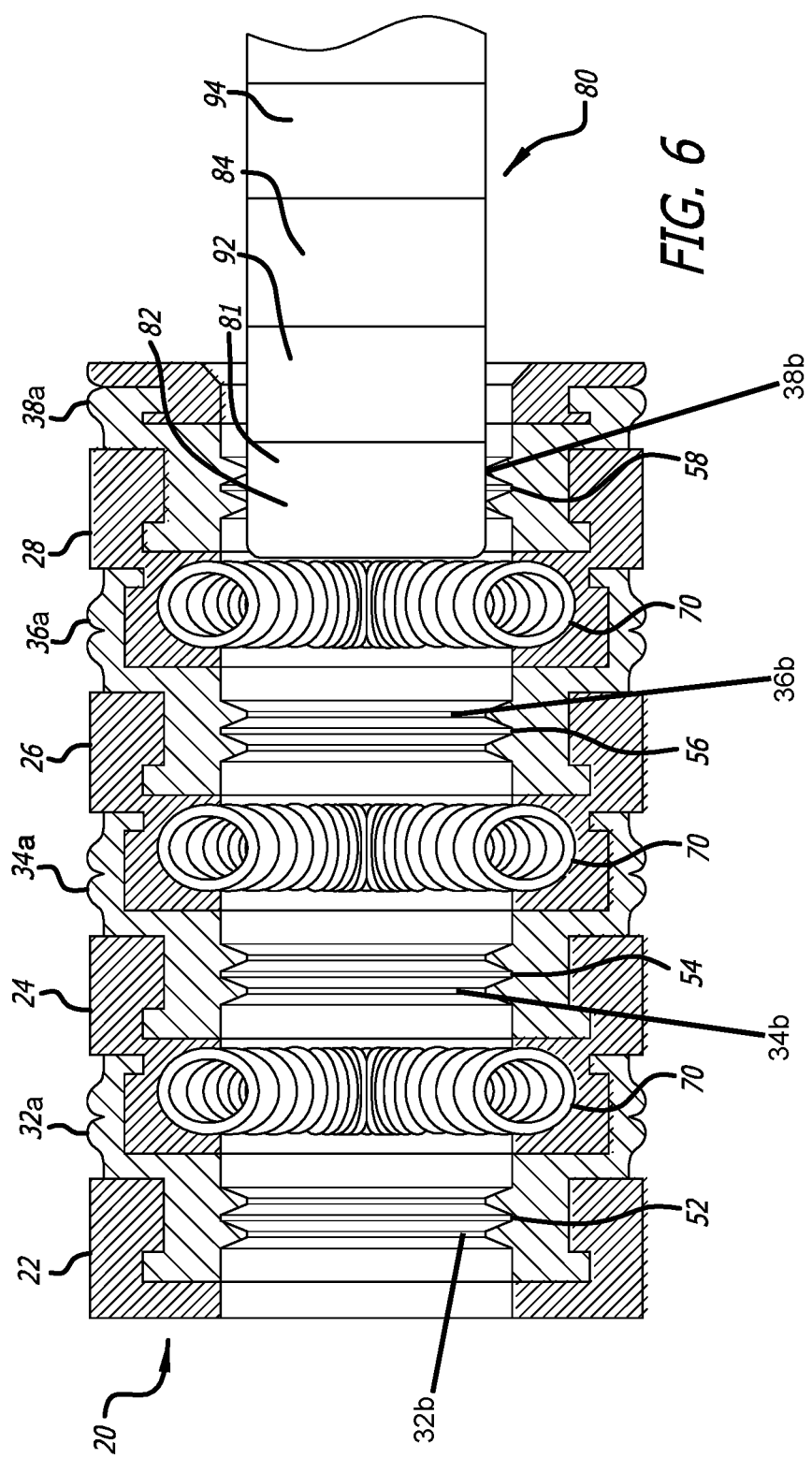
FIG. 6 is a detailed cutaway view of an embodiment of an integral wiping system of the invention.
Figure 7:
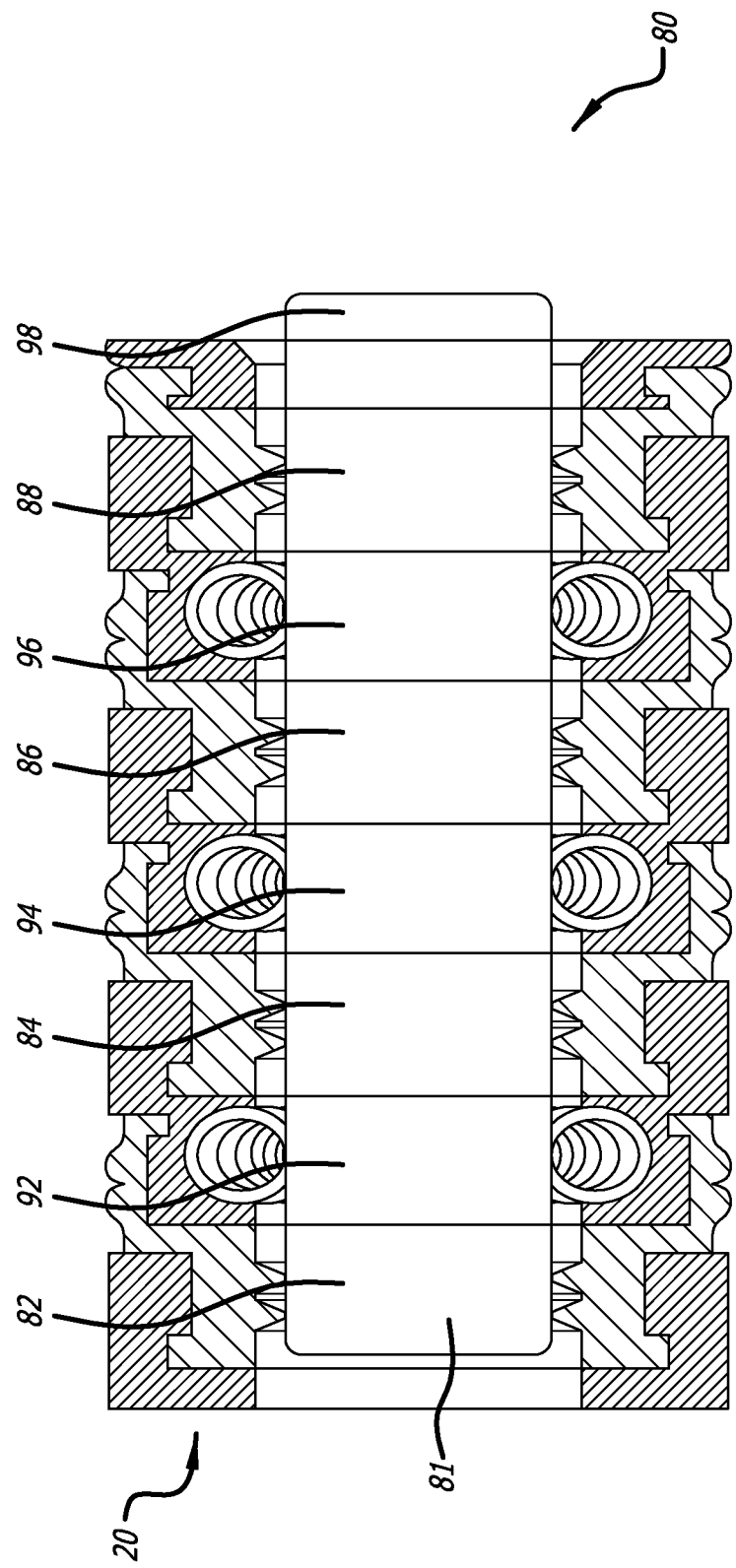
FIG. 7 is a detailed cutaway view of an embodiment of an integral wiping system of the invention.

FIGS. 6-7 illustrate the interface between pusher/grip connector 20 and pusher system 80. FIG. 6 shows the pusher/grip connector 20 and the series of channels 22, 24, 26, 28. The channels contain a series of contacts 52, 54, 56, 58 respectively housed in each channel. Contacts 52, 54, 56 and 58 each have surfaces 32a, 34a, 36a and 38a, which are in turn connected to contact bumps 32, 34, 36 and 38 of circuit board 44 as a part of control system 30. Contacts 52, 54, 56 and 58 also have inner continuous circumferential surfaces 32b, 34b, 36b and 38b, which are configured to contact the surfaces 82, 84, 86 and 88 of the pusher system 80 when inserted therein.

The user inserts pusher system 80 into the pusher/grip connector 20. The proximal end of pusher system 80 is pushed into pusher/grip connector 20 of grip system 10, while a distal end of the pusher system sits within the vasculature system. The distal end of pusher system 80 is connected to an embolic agent, such as embolic coil (not shown). At a more distal portion of the pusher system, a release agent such as a heater coil can be used to release the embolic coils from the pusher system when desired. The heater coil would heat a junction between pusher system 80 and the embolic coil, causing the coils to sever and detach within the vasculature.

Pusher system 80 has a number of contacts 82, 84, 86, 88 which mate with corresponding contacts 52, 54, 56, 58 of the pusher/grip connector 20 in a male/female relationship. Pusher system 80 may have a number of blank leads 92, 94, 96, 98 which sit between contacts 82, 84, 86, 88. These blank leads correspond to sections of pusher/grip connector 20 which do not have contacts. Alternatively, pusher system 80 may have a solid contact block which interfaces with contacts 52, 54, 56, 58. In one example pusher system 80 is comprised of one solid contact block made of stainless steel with gold plating. In another example contact sections 82, 84, 86, 88 are made of stainless steel with gold plating and sections 92, 94, 96, 98 have an epoxy coating. In another example sections 82, 84, 86, 88, 92 are made of stainless steel with gold plating and the rest of the sections have an epoxy coating. In another example sections 82, 84, 86, 88, 92, 98 are made of stainless steel with gold plating and the rest of the sections have an epoxy coating. Although FIGS. 6-7 show four contacts within pusher/grip connector 20 and four contacts on pusher system 80, more or fewer contacts can be used.

Sections of pusher/grip connector 20 which do not have contacts have wipers 70 filling the space. Ordinarily, any fluid accumulation on any section of pusher system 80 can result in deterioration of connection integrity between the pusher contacts and the pusher/grip contacts. Deterioration in connection integrity can cause the detachment sequence to not initiate properly. The user may be able to manually wipe the leads 80 to remove any liquid, however, the wiping apparatus the user uses may be corrupted with liquid (such as blood or saline). Wipers 70 wipe away any liquid which may accumulate on pusher system 80, thus reducing the chance of the connection integrity failing, thus reducing the chance of the detachment sequence not initiating properly. The wipers may be made out of materials which promote absorption of typical contaminating liquids such as saline and blood. Absorbable substances such as paper, cloth, sponge, or polymeric material could be used. The wipers may take on a plurality of shapes, i.e. circular, ellipsoid, rectangular, square, triangular, polygonal, etc. In addition, various combinations of materials and shapes can be used for the wipers to customize the wiping capability of each section.

In FIGS. 6-7, three wipers are used corresponding to the sections which sit between contacts 52, 54, 56, 58. Such a configuration is offered only as an example. In the particular configuration shown, the wiper elements are arranged in alternating fashion with the electrical contacts such that a first wiper element is located proximally of the first electrical contact at the distal end of the handle, such that the wipers sequentially wipe each portion of the pusher system 80 that is pushed through the wipers, thus minimizing the chance of fluid buildup which can degrade the electrical connection system. More or fewer wipers can be used (i.e. in the three-section configuration shown, the proximal and distal end sections may utilize a wiper while the middle section does not, or just the middle and distal end section portion, or a wiper may be utilized on only one of the proximal/distal/middle sections, etc.) Fewer wipers may be utilized in a situation where highly absorbent material is used. The wiper size may also vary (i.e. filling just a portion of the section it sits in, or filling substantially all of the section if sits in). This size can vary both in height and in width. Additionally, the number of sections may vary from one to more than three, and the wipers in turn can sit within one or more sections. Additionally, more than one wiper can be used in each section.

Preferably, the wipers 70 are annular coils, as shown, and sized to place a moderate amount of pressure on the pusher system 80 when the proximal end 81 of the pusher system 80 is inserted into pusher/grip connector 20. This friction fit ensures an efficient cleaning of the pusher system 80 as it is inserted. Additionally, the use of multiple wipers 70 further protects the inner components of the pusher/grip connector 20 from contamination.

A typical operation of the device is as follows. The user would insert a proximal end 81 of pusher system 80 into the pusher/grip connector 20 of grip system 10, as shown in FIG. 6. As the proximal end of pusher system is inserted into the pusher/grip connector 20, fluid present on any section of pusher system 80 would be wiped from the pusher by wipers 70. As shown in FIG. 7, when the pusher system 80 is correctly aligned within pusher/grip connector 20, contact sections 82, 84, 86, 88 of the pusher system will directly align with contacts 52, 54, 56, 68 of the pusher/grip connector. Connectors 32, 34, 36, 38—which are connected respectively to contacts 52, 54, 56, 58—will convey a signal when the pusher contacts 82, 84, 86, 66 are aligned with pusher/grip connector contacts 52, 54, 56, 68. If the respective connectors are aligned correctly, the signal will be conveyed through connectors 32, 34, 36, 38 via control system 30. Light 48 will subsequently light up a particular color (i.e. green), indicating that a detachment sequence can be initiated. To initiate the detachment sequence the user pushes button 16. Pushing button 16 will initiate depression of back button 46 which sits behind button 16. This will result in detachment of the embolic coils from pusher system 80 at a more distal portion of pusher system 80. In one example, pushing button 16 initiates the heating of a heater coil at a more distal portion of pusher system 80, where pusher system 80 is connected to an embolic coil. This heating will result in detachment of the embolic coil from the pusher system. Thus the embolic coil will be detached within the target area of the vasculature.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A grip assembly for a medical delivery system, comprising:

a housing having a top portion and a bottom portion forming a space within said housing;

a circuit board positioned within said space within said housing;

a power supply positioned within said space within said housing and electrically connected to said circuit board;

an electrical actuation button electrically connected to said circuit board;

an indicator electrically connected to said circuit board and being exposed on an exterior of said housing;

a funnel portion disposed on a distal end of said housing; and a channel positioned within said space within said housing and having an opening outside of said housing and at said funnel portion; said channel comprising:

a plurality of electrical contact members comprising a first electrical contact member, a second electrical contact member, a third electrical contact member, and a fourth electrical contact member; each of which have a first inner diameter and a first outer diameter; said first outer diameter being in contact with said circuit board;

a plurality of channel members, each being disposed between two of said plurality of electrical contact members;

a plurality of wiper elements each of which is fixed to an inner surface of said plurality of channel members; said plurality of wiper elements each having a second inner diameter that is smaller than said first inner diameter of said plurality of electrical contacts, and that further is sized to create a friction fit with a proximal end of a pusher; said plurality of wiper elements comprising coils having an annular shape and including a liquid-absorbing material;

wherein said plurality of wiper elements are arranged in alternating fashion with said plurality of electrical contacts such that a distalmost wiper element is located proximally of a distalmost electrical contact at the distal end of said housing;

wherein said circuit board illuminates said indicator in a first color when a plurality of pusher contacts on said pusher are aligned with said plurality of electrical contacts, and illuminates said indicator in a second color when said plurality of pusher contacts on said pusher are not aligned with said plurality of electrical contacts.

* * * * *